(12) United States Patent
Bon et al.

(10) Patent No.: US 9,499,507 B2
(45) Date of Patent: *Nov. 22, 2016

(54) METHOD FOR PREPARING 5-AMINO-BENZOYL-BENZOFURAN DERIVATIVES

(71) Applicant: Sanofi, Paris (FR)

(72) Inventors: Xavier Bon, Paris (FR); Jean-Louis Delepine, Paris (FR); Laure Jourdin, Paris (FR); Denis Largeau, Paris (FR); Philippe Vayron, Paris (FR)

(73) Assignee: SANOFI, Paris (FR)

( * ) Notice: Subject to any disclaimer, the term of this patent is extended or adjusted under 35 U.S.C. 154(b) by 1 day.

This patent is subject to a terminal disclaimer.

(21) Appl. No.: 14/361,562

(22) PCT Filed: Nov. 28, 2012

(86) PCT No.: PCT/FR2012/052735
§ 371 (c)(1),
(2) Date: May 29, 2014

(87) PCT Pub. No.: WO2013/079866
PCT Pub. Date: Jun. 6, 2013

(65) Prior Publication Data
US 2015/0031901 A1 Jan. 29, 2015

(30) Foreign Application Priority Data
Nov. 29, 2011 (FR) ........................... 11 60901

(51) Int. Cl.
*C07D 307/78* (2006.01)
*C07D 307/80* (2006.01)
*C07D 307/82* (2006.01)

(52) U.S. Cl.
CPC ........... *C07D 307/80* (2013.01); *C07D 307/82* (2013.01)

(58) Field of Classification Search
CPC ............... C07D 209/14; C07D 209/12; C07D 307/78; C07D 307/80; C07D 307/82
USPC ........................................ 549/467
See application file for complete search history.

(56) References Cited

U.S. PATENT DOCUMENTS

| | | | |
|---|---|---|---|
| 3,577,441 A | 5/1971 | Kaminsky et al. | |
| 3,657,350 A | 4/1972 | Mooradian et al. | |
| 3,937,737 A | 2/1976 | Eiglmeier | |
| 4,243,405 A | 1/1981 | Balasubramanyan et al. | |
| 4,666,931 A | 5/1987 | Ohishi et al. | |
| 5,066,803 A | 11/1991 | D'Ambra et al. | |
| 5,223,510 A | 6/1993 | Gubin et al. | |
| 6,555,697 B1 | 4/2003 | Schlama | |
| 6,828,448 B2 | 12/2004 | Fino et al. | |
| 6,846,936 B2 | 1/2005 | Biard | |
| 6,855,842 B1 | 2/2005 | Schlama et al. | |
| 6,949,583 B2 | 9/2005 | Assens et al. | |
| 6,984,741 B2 | 1/2006 | Magerlein | |
| 7,148,240 B2 | 12/2006 | Assens et al. | |
| 7,312,345 B2 | 12/2007 | Gutman et al. | |
| 7,517,876 B2 | 4/2009 | Klein et al. | |
| 8,143,269 B2 | 3/2012 | Whitten et al. | |
| 8,501,971 B2 | 8/2013 | Friesz et al. | |
| 8,658,808 B2 | 2/2014 | Kretzschmar et al. | |
| 8,658,809 B2 | 2/2014 | Friesz et al. | |
| 8,674,121 B2 | 3/2014 | Kretzschmar et al. | |
| 8,686,180 B2 | 4/2014 | Bon et al. | |
| 8,748,636 B2 | 6/2014 | Bailly et al. | |
| 8,796,489 B2 | 8/2014 | Bailly et al. | |
| 8,816,103 B2 | 8/2014 | Friesz et al. | |
| 8,871,956 B2 | 10/2014 | Bailly et al. | |
| 8,884,033 B2 * | 11/2014 | Bon ..................... | A61K 31/343 549/468 |
| 8,889,734 B2 | 11/2014 | Friesz et al. | |
| 8,927,743 B2 | 1/2015 | Vishnu Newadkar et al. | |
| 8,962,869 B2 | 2/2015 | Grimaud et al. | |
| 9,024,046 B2 | 5/2015 | Friesz et al. | |
| 9,174,958 B2 | 11/2015 | Friesz | |
| 9,174,959 B2 | 11/2015 | Friesz et al. | |
| 9,238,636 B2 | 1/2016 | Huszar et al. | |
| 2008/0033209 A1 | 2/2008 | Szarvas et al. | |
| 2010/0087415 A1 | 4/2010 | Whitten et al. | |

(Continued)

FOREIGN PATENT DOCUMENTS

CN 101838252 A 9/2010
CN 101993427 A 3/2011
(Continued)

OTHER PUBLICATIONS

Li et al, Synthesis of dronedarone hydrochloride, Zhongguo Yiyao Gonye Zazhi, 2011, 42(3), p. 161-164, (7 pages).*
International Search Report dated Jan. 23, 2013 issued in PCT/FR2012/052735.
Abramenko et al. (1975). "Polymethine Dyes—Furo[2,3-g] Benzothiazole Derivatives," Chemistry of Heterocyclic Compounds 11:1361-1364.
Adams et al. (1951). Quinone imides. IV. P-Quinone monosulfonimides. Journal of the American Chemical Society 73:1145-1149.
Adams et al. (1956). "Quinone Imides. XXXIX. Adducts of Quinone Monoimides and Conversion of Active Methylene Adducts to Benzofurans," *J. Am. Chem. Soc.* 78(3):658-663.

(Continued)

*Primary Examiner* — T. Victor Oh
(74) *Attorney, Agent, or Firm* — Morrison & Foerster LLP

(57) ABSTRACT

The invention relates to a method for preparing 5-amino-benzoyl-benzofuran derivatives having the general formula in which $R_1$ is hydrogen or an alkyl or aryl group and $R_2$ is hydrogen, an alkyl, alkoxy or dialkylaminoalkoxy group. According to the invention, the compounds having formula I are prepared by hydrogenating a 5-nitro-benzofuran derivative having the general formula in which $R_1$ and $R_2$ have the same meaning as above in the presence of palladized charcoal as a catalyst and in an ether or a mixture of ether as a solvent, thus forming the desired compounds.

25 Claims, No Drawings

(56) References Cited

U.S. PATENT DOCUMENTS

| | | |
|---|---|---|
| 2010/0273764 A1 | 10/2010 | Andrews et al. |
| 2013/0023678 A1 | 1/2013 | Priem et al. |
| 2013/0109868 A1 | 5/2013 | Friesz |
| 2014/0018553 A1 | 1/2014 | Grimaud et al. |
| 2014/0081035 A1 | 3/2014 | Friesz et al. |
| 2014/0114081 A1 | 4/2014 | Friesz et al. |
| 2015/0005515 A1 | 1/2015 | Friesz et al. |
| 2015/0018568 A1 | 1/2015 | Friesz |
| 2015/0031902 A1 | 1/2015 | Huszar et al. |
| 2016/0009678 A1 | 1/2016 | Husz r et al. |
| 2016/0009679 A1 | 1/2016 | Friesz et al. |
| 2016/0075673 A1 | 3/2016 | Friesz |
| 2016/0075674 A1 | 3/2016 | Friesz et al. |

FOREIGN PATENT DOCUMENTS

| | | |
|---|---|---|
| EP | 0 471 609 A1 | 2/1992 |
| EP | 0 735 083 A1 | 10/1996 |
| ES | WO2007/116111 * | 10/2007 |
| FR | 2 833 259 A1 | 6/2003 |
| GB | 1064959 * | 4/1967 |
| WO | WO-96/05190 A1 | 2/1996 |
| WO | WO 02/48078 A1 | 6/2002 |
| WO | WO-02/48132 A1 | 6/2002 |
| WO | WO-03/040120 A1 | 5/2003 |
| WO | WO-2005/012301 A1 | 2/2005 |
| WO | WO-2007/022501 A2 | 2/2007 |
| WO | WO-2007/022501 A3 | 2/2007 |
| WO | WO-2007/100295 A1 | 9/2007 |
| WO | WO-2007/133637 A2 | 11/2007 |
| WO | WO-2007/133637 A3 | 11/2007 |
| WO | WO-2007/140989 A2 | 12/2007 |
| WO | WO-2007/140989 A3 | 12/2007 |
| WO | WO-2009/044143 A2 | 4/2009 |
| WO | WO-2009/044143 A3 | 4/2009 |
| WO | WO-2010/038029 A1 | 4/2010 |
| WO | WO-2010/040261 A1 | 4/2010 |
| WO | WO-2010/116140 A1 | 10/2010 |
| WO | WO-2010/136500 A1 | 12/2010 |
| WO | WO-2010/136502 A1 | 12/2010 |
| WO | WO 2011/070380 A1 | 6/2011 |
| WO | WO-2011/099010 A1 | 8/2011 |
| WO | WO 2011/104591 A1 | 9/2011 |
| WO | WO-2011/107705 A1 | 9/2011 |
| WO | WO-2011/158050 A1 | 12/2011 |
| WO | WO-2012/004658 A2 | 1/2012 |
| WO | WO-2012/004658 A3 | 1/2012 |
| WO | WO-2012/010788 A1 | 1/2012 |
| WO | WO-2012/010802 A1 | 1/2012 |
| WO | WO-2012/010913 A1 | 1/2012 |
| WO | WO-2012/032545 A1 | 3/2012 |
| WO | WO-2012/127173 A1 | 9/2012 |
| WO | WO-2012/131408 A1 | 10/2012 |
| WO | WO-2012/131409 A1 | 10/2012 |
| WO | WO-2012/131410 A1 | 10/2012 |
| WO | WO-2013/014478 A1 | 1/2013 |
| WO | WO-2013/014479 A1 | 1/2013 |
| WO | WO-2013/014480 A1 | 1/2013 |
| WO | WO-03/048144 A2 | 6/2013 |
| WO | WO-03/048144 A3 | 6/2013 |
| WO | WO-2013/121234 A1 | 8/2013 |
| WO | WO-2013/121235 A2 | 8/2013 |
| WO | WO-2013/121235 A3 | 8/2013 |
| WO | WO-2013/128294 A2 | 9/2013 |
| WO | WO-2013/128294 A3 | 9/2013 |
| WO | WO-2013/128294 A8 | 9/2013 |

OTHER PUBLICATIONS

Alcaraz et al. (2004). "Novel N-Aryl and N-Heteroaryl Sulfamide Synthesis via Palladium Cross Coupling," Organic Letters 6(16):2705-2708.

Ando et al. (1982). "Motion at the Active Site of Tosylchymotrypsin," Journal of the American Chemical Society 104(11):3172-3178.

Anjanappa et al. (2008). "2-(Trimethylsilyl)ethanesulfonyl amide as a new ammonia equivalent for palladium- catalyzed amination of aryl halides," Tetrahedron Letters 49:4585-4587.

Bartoli et al. (1991). "Unexpected Elimination to α,β-Alkynylketones in the Reaction of Dianions of 1-Arylenaminones with Trimethylchlorosilane," Tetrahedron Letters 32(48):7091-7092.

Batra et al. (2001). "Syntheses and Biological Evaluation of Alkanediamines as Antioxidant and Hypolipidemic Agents," Bioorganic & Medicinal Chemistry 9(12):3093-3099.

Bavin (1973). "2-Aminofluorene," Org. Syn. Coll. 5:30.

Berthold et al. (2002). "Transfer Hydrogenation in Ionic Liquids under Microwave Irradiation," Syn. 1607-1610.

Boovanahalli et al. (2004). "Application of Ionic Liquid Halide Nucleophilicity for the Cleavage of Ethers: A Green Protocol for the Regeneration of Phenols from Ethers," Journal of Organic Chemistry 69:3340-3344.

Bourgery et al. (1981). "Synthesis and Antiarrhythmic Activity of New Benzofuran Derivatives," Journal of Medicinal Chemistry 24(2):159-167.

Burton et al. (2003). "Palladium-Catalyzed Intermolecular Coupling of Aryl Chlorides and Sulfonamides under Microwave Irradiation," Organic Letters 5(23):4373-4376.

Castellino et al. (1984). "Synthesis of Benzofurans from Oxygenated Phenoxyamines," Journal of Organic Chemistry 49:4399-4404.

Chauhan et al. (2004). "Microwave assisted dealkylation of alkyl aryl ethers in ionic liquids," Journal of Chemical Research, pp. 693-694.

Cheng et al. (2007). "Facile Cleavage of Ethers in Ionic Liquid," Bulletin of the Chemical Society of Japan 80(10):2008-2010.

Database PubChem Compound [Online] (Oct. 25, 2006),"CID 10095002—Compound Summary:N-[3-[4-(3-aminopropoxy)benzoyl)-2-butyl-1-benzofuran-5-yl", XP002676507, Database accession No. 15082344. Retrieved from the Internet: URL:http://pubchem.ncbi.nlm.nih.gov/summary/summary.cgi?sid=15082344&viewopt=PubChem [retrieved on May 23, 2012].

Delahay et al. (2007). "Past and Recent Approaches of Preparing Fe-ZSM-5," Current Topics in Catalysis 6:19-33.

Douglass (1959). "Some New Reactions of Methanesulfenyl Chloride," Journal of Organic Chemistry 24:2004-2006.

Denmark et al. (2008). "Lewis base catalysis in organic synthesis," Angew. Chem. Int. Ed. 47(9):1560-1638.

Fennel (1958). "Quinoline Analogs of Podophyllotoxin. I. Preliminary Experiments. Syntheses of Some 4-Phenylquinoline Derivatives," J. Org. Chem. 23:432-434.

Fieser et al. (1967). "Reagents for Organic Synthesis," John Wiley & Sons, pp. 703-705.

Fontana (2008). "Syntheses of (R,S)-Naproxen and its 6-O-Desmethyiated metabolite labelled with 2H," J. Labelled Compounds and Radiopharma. 51:239-241.

Gilow et al. (Jun.-Jul. 1991). "Sulfenylation of Some Pyrroles and Indoles," J. Het. Chem. 28:1025-1034.

Groves (1972). "The Friedel—Crafts Acylation of Alkenes," Chem. Soc. Rev. 1:73-97.

Gutowski et al, (2005). "Prediction of the Formation and Stabilities of Energetic Salts and Ionic Liquids Based on ab lnitio Electronic Structure Calculations," The Journal of Physical Chemistry B 109:23196-23208.

Haddadin et al. (1976). "Reaction to Benzofurazan Oxide with Unsymmetrical 1, 3-Diketones: Steric Polar Effects," Tetrahedron 32:719-724.

Hauser et al. (1948) "Alkaline cleavage of unsymmetrical β-diketones. Ring opening of acylcyclohexanones to form ε-acylcaproic acids," Journal of the American Chemical Society. 70:4023-4026.

Headley et al. (2006). "Dynamic Solvation in Imidazolium-Based Ionic Liquids on Short Time Scales," Journal of Physical Chemistry 110:9549-9554.

Horton et al. (1967). "Reactions With Reactive Alkyl Halides," J. Meth. In Enzymology 11:556-565.

Ikawa et al. (2007). "Pd-Catalyzed Amidations of Aryl Chlorides Using Monodentate Biaryl Phosphine Ligands: A Kinetic, Compu-

(56) References Cited

OTHER PUBLICATIONS tational, and Synthetic Investigation," Journal of the American Chemical Society 129:13001-13007.
Imori et al. (2006). "Efficient Demethylation of N,N-Dimethylanilines with Phenyl Chloroformate in Ionic Liquids," Synlett. 16:2629-2632.
Johnson Matthey Handbook of Pharmaceutical Catalysis, 2009, pp. 1-106.
Joshi et al. (1986). "Some New Fluorinated β-Ketoamines and Their Copper Complexes," Synth. React. Inorg. Met. -Org. Chem. 16(7):1009-1024.
Krongauz et al. (1986). Poly(anilophenylquinoxaline)s. Inst. Elementoorg. Soedin. 28(4):771 (Abstract).
Kurti et al. (2005). Strategic Applications of Named Reactions in Organic Synthesis. El Sevior, pp. 448-449.
Kwiatkowski et al. (1978). "Metal Benzoylpivaloylmethanates, Part I. Free Ligands and Copper(II) Chelates," Transition Met. Chem. 3:305-308.
Laszlo et al. (1987). "Catalysis of Friedel-Crafts Alkylation by a Montmorillonite Doped with Transition-Metal Cations," Helvetica Chimica Acta 70:577-586.
Liu et al. (2004). "Cleavage of Methyl Ethers of Flavones by Chloroaluminate Ionic Liquid," Synthetic Communications 34:3209-3218.
Majdik (1985). "Studiul reactiei de ciclizare a orto-hidroxibenzilfenilcetonelor in benzofuran derivati," Revista de Chimie 36(8):760-761 (with English Translation).
Majdik et al. (1989). "Prepararea unor 2-(aril)-nitrobenzofurani din 0-(nitrofenil)-acetofenonoxime," Revista de Chemie, vol. 40, No. 8, pp. 689-693 (with English Translation).
Majdik et al. (1989). "0-Arilarea cetoximelor cu nitroclorbenzeni," Revista de Chemie, vol. 40, No. 6, pp. 490-493 (with English Translation).
March (Jul. 1, 1992). "Aromatic Electrophilic Substitution," Chapter 11 in *Advanced Organic Chemistry, Reactions, Mechanism and Structure*, 4th edition, Wiley Interscience, pp. 538-542.
March (Jul. 1, 1992). "Aliphatic Nucleophilic Substitution," Part 2 in *Advanced Organic Chemistry, Reactions, Mechanism and Structure*, 4th edition, Wiley Interscience, pp. 442.
Marvel et al. (1941). "Diphenylacetic Acid," Org. Synth. Coll. vol. 1, 224-225.
Mehrotra et al. (2001). "Search for new chemical entities as menses inducing agents," Contraception. 64:187-191.
Munch et al. (1946). "The Preparation of Some α-Dialkylamino-ω-Methylaminoalkanes," J. Am. Chem. Soc. 68:1297-1299.
Nagy et al. (2007). "Isomorphous Substitution in Zeolites," Mol. Sieves 5:365-478.
Nakamura et al. (2004). "Pyrazole Derivatives as new potent and selective 20-hydroxy-5,6,11,14-Eicosatetraenoic Acid Synthase Inhibitors," Bioorganic Medic. Chem. 12:6209-6219.
Pal et al. (2007). "Synthesis of monohydroxy-functionalized triphenylene discotics: green chemistry approach," Tetrahedron 63:6874-6878.
Roshchin et al. (1998). "Synthesis of Benzofurans via Pd2+-Catalyzed Oxidative Cyclization of 2-Allylphenols," Journal of Organometallic Chemistry 560(1-2):163-167.
Sanfilippo (1988). "Synthesis of (aryloxy)alkylamines. 1. Novel antisecretory agents with H+K+-ATPase inhibitory activity," J. Med. Chem. 31(9):1778-1785.
Serajuddin (2007). "Salt formation to improve drug solubility," Advanced Drug Delivery Reviews 59:603-616.
Shridhar (1981). "Synthesis & Biological Activity of Some New 2-[(5-Nitro-2-furyl- & 5-nitro-2-thienyl)vinyl]-N-arylsulphonamides & 1-[2-(5-Nitro-2-furyl & 5-nitro-2-thienyl)vinyl]sulphonyl Heterocycles," Indian Journal of Chemistry 208:234-237.
Skeels et al. (1989). "Zeolite Chemistry, Substitution of iron or titanium for Aluminum in Zeolites via reaction with the respective ammonium fluoride salts," *ACS Symposium series, zeolite Synthesis* 398:420-435.
Ślusarska et al. (Feb. 1981). "One-Pot Phase-Transfer-Catalysed N-Alkylation of Diphenylphosphinamide with Alcohols in the Presence of Methanesulfonyl Chloride," Synthesis 155-156.
Son et al. (1989). "Stereochemical Mechanism of Iodoacetic Acid Mediated Decomposition of $_L$-Methionine to $_L$-Homoserine Lactone," Journal of the American Chemical Society 111(4):1363-1367.
Sun et al. (2004). "N-{2-[2-( 4-Phenylbutyl)benzofuran-4-yl]cyclopropylmethyl}-acetamide: an orally bioavailable melatonin receptor agonist," Bioorganic & Medicinal Chemistry Letters 14:5157-5160.
Tanaka (1967). Studies on 5-Aminosalicylaldehyde Derivatives. II. Reduction of 5-(p-Sulfophenylazo)salicylaldehyde Through Poly(5-Nitrilosalicylidene) to 5-Aminosalicylaldehyde Derivatives, Bulletin of the Chemical Society of Japan 40(7):1724-1726.
Thornber (1979). "Isosterism and molecular modification in drug design." Chem. Soc. Rev. 8:563-580.
Upthagrove et al. (Nov. 2001). "Importance of Amine $pK_a$ and Distribution Coefficient in the Metabolism of Fluorinated Propranolol Derivatives. Preparation, Identification of Metabolite Regioisomers, and Metabolism by CYP2D6," Drug Metab. Dispos. 29(11):1377-1388.
Wamser et al. (1989). "Kinetics and Mechanisms for the Two-phase Reaction between Aqueous Aniline and Benzoyl Chloride in Chloroform, with and without Pyridine Catalysis," J. Org. Chem. 54:150-154.
Weissman et al. (2005). "Recent advances in ether dealkylation," Tetrahedron 61:7833-7863.
Weitkamp et al. (1986). "Isomorphe Substitution in Zeolithen: Katalyse an Boro-, Alumo-und Galio-Silicaten mit ZSM-5-Strukter," Chem. Ing. Tech. 58(12):969-971 (with English Translation).
Wikipedia. (Nov. 5, 2012). "Reduction of Nitro Compounds."
Wu et al. (2004). "Immobilization of HX: [Hmim]X as Halogenating Agent, Recyclable Catalyst and Medium for Conversion of Alcohols to alkyl halides," Chinese J. Chem. 22:619-621.
Wuts (2006). Greene's Protective Groups in Organic Synthesis, Fourth Edition, John Wiley and Sons, Chapter 7, Protection for the Amino Group, pp. 696-926.
Yang et al. (2009). "Structure-based virtual screening for identification of novel 11 β-HSD1 inhibitors," European J. of Medicinal Chem. 44(3):1167-1171.
Yin et al. (2000). "Palladium-Catalyzed Intermolecular Coupling of Aryl Halides and Amides," Organic Letters 2(8):1101-1104.
Yin et al. (2002). "Pd-Catalyzed Intermolecular Amidation of Aryl Halides: The Discovery that Xantphos Can Be Trans-Chelating in a Palladium Complex," Journal of the American Chemical Society 124:6043-6048.
Zasshi (1956). "Studies on the Syntheses of Phenothiazine Derivatives. I. Syntheses of N-Substituted Phenothiazines by Tosylates," J. Pharm. Soc. of Japan 76:637-640 (with English Translation).
U.S. Appl. No. 14/377,484, filed Aug. 7, 2014, by Huszar et al.
U.S. Appl. No. 14/403,528, filed Nov. 24, 2014, by Huszar et al.
Stahl, P.H. et al. (2005). "List of Pharmaceutically Acceptable Acids," The Royal Society of Chemistry in *Handbook of Pharmaceutical Salts: Properties, Selection and Use*, Electronic Supplementary Material for CrystEngComm, one page.
U.S. Appl. No. 14/945,222, filed Nov. 18, 2015, by Friesz et al.
U.S. Appl. No. 14/946,510, filed Nov. 19, 2015, by Friesz et al.
Landge et al. (2013) "Stability Indicating RP-HPLC Method for the Determination of Dronedarone Hydrochloride and its Potential Process-Related Impurities in Bulk Drug and Pharmaceutical Dosage Form," American Journal of Analytical Chemistry 4:323-335.

* cited by examiner

METHOD FOR PREPARING 5-AMINO-BENZOYL-BENZOFURAN DERIVATIVES

The present invention relates generally to the preparation of amino-benzoyl-benzofuran derivatives.

More specifically, the invention relates to a process for the preparation of 5-amino-benzoyl-benzofuran derivatives of general formula:

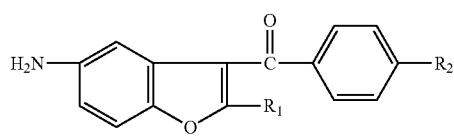

in which $R_1$ represents hydrogen or an alkyl or aryl group and $R_2$ represents hydrogen or an alkyl, alkoxy or dialkylaminoalkoxy group, In the above formula I:

$R_1$ represents in particular a linear or branched $C_1$-$C_8$ alkyl group, in particular a linear or branched $C_1$-$C_4$ alkyl group, such as methyl, ethyl, n-propyl, isopropyl, n-butyl, sec-butyl or tert-butyl, or else a substituted or unsubstituted phenyl group, $R_2$ represents in particular a linear or branched $C_1$-$C_8$ alkyl group, in particular a linear or branched $C_1$-$C_4$ alkyl group, such as methyl, ethyl, n-propyl, isopropyl, n-butyl, sec-butyl or tert-butyl; a linear or branched $C_1$-$C_8$ alkoxy group, in particular a linear or branched $C_1$-$C_4$ alkoxy group, such as methoxy, ethoxy, n-propoxy, isoproxy, n-butoxy, sec-butoxy or tert-butoxy; or else a dialkylaminoalkoxy group in which each linear or branched alkyl group is a $C_1$-$C_8$ alkyl group and the linear or branched alkoxy group is a $C_1$-$C_8$ alkoxy group, in particular in which each linear or branched alkyl group is a $C_1$-$C_4$ alkyl group, such as methyl, ethyl, n-propyl, isopropyl, n-butyl, sec-butyl or tert-butyl, and the linear or branched alkoxy group is a $C_1$-$C_4$ alkoxy group, such as methoxy, ethoxy, n-propoxy, isopropoxy, n-butoxy, sec-butoxy or tert-butoxy.

According to one embodiment, $R_1$ represents n-butyl and $R_2$ represents 3-[di(n-butyl)amino]propoxy.

The compounds of formula I above are, for the most part, compounds described in patent EP 0 471 609, where they are presented as intermediates in the final preparation of aminoalkoxybenzoyl-benzofuran derivatives of use for their therapeutic applications in the cardiovascular field.

Among these aminoalkoxybenzoyl-benzofuran derivatives, 2-(n-butyl)-3-(4-{3-[di(n-butyl)amino]propoxy}benzoyl)-5-(methanesulfonamido)benzofuran, commonly referred to as dronedarone, and its pharmaceutically acceptable salts, has proven to be particularly advantageous, in particular as antiarrhythmic agent.

A process for the preparation of dronedarone was reported in the abovementioned patent EP 0 471 609, according to which 2-(n-butyl)-3-(4-{3-[di(n-butyl)amino]propoxy}benzoyl)-5-nitrobenzofuran is reduced under pressure with hydrogen in the presence of platinum oxide as catalyst to form 2-(n-butyl)-3-(4-{3-[di(n-butyl)amino]propoxy}benzoyl)-5-aminobenzofuran (hereinafter Compound A), which is subsequently treated with methanesulfonyl chloride, in the presence of an acid acceptor, to give the desired compound. According to this process, dronedarone could be obtained with an overall yield of the order of 60%, starting from the 5-nitrobenzofuran derivative.

Thus, the purity of Compound A obtained after hydrogenation is not sufficient to envision a direct linking of the steps in the same reactor, which results in a lower overall yield. Indeed, the hydrogenation as presented above results in the formation of impurities resulting in particular from the reduction of the ketone functional group.

Consequently, on an industrial scale, this method requires the isolation of Compound A from its formation medium, the isolation of this compound, normally in the form of its oxalate, consequently constituting an additional step in the preparation of dronedarone.

The search for an industrial preparation process capable of overcoming these disadvantages while offering high yields of Compound A and also facilitated use of the latter, so as to produce significantly greater yields of dronedarone with respect to the prior process, consequently remains of indisputable interest.

In point of fact, it has now been found that Compound A can be prepared according to a process involving a selective reduction of the nitro functional group with respect to the ketone functional group. This selective reduction makes it possible to obtain a sufficient purity of Compound A and consequently eliminates the need to isolate this Compound A via its oxalate and makes it possible to link the steps up to dronedarone, which can thus be prepared and isolated with overall yields of greater than 90% from the starting 5-nitrobenzofuran derivative.

The aminoalkoxybenzoyl-benzofuran derivatives of patent EP 0 471 609, in particular dronedarone, can consequently be synthesized in the very medium for formation of the appropriate compound of formula I.

According to a first subject of the invention, the 5-aminobenzofuran derivatives of formula I can be prepared by hydrogenating a 5-nitrobenzofuran derivative of general formula:

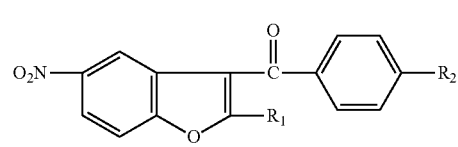

in which $R_1$ and $R_2$ have the same meanings as above, in the presence of palladium-on-charcoal as catalyst and in an ether or a mixture of ethers as solvent, which forms the desired compounds.

In the above formula II, $R_1$ more particularly represents n-butyl and $R_2$ preferably represents 3-[di(n-butyl)amino]propoxy.

In addition, according to another of its subjects, the invention relates to a process for the preparation of sulfonamidobenzofuran derivatives of general formula:

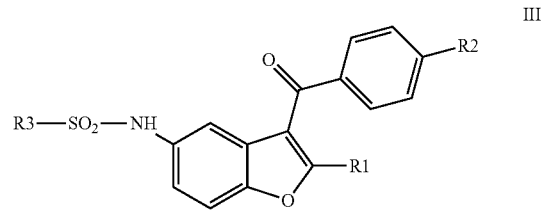

and of their pharmaceutically acceptable salts, in which $R_1$ and $R_2$ have the same meanings as above and $R_3$ represents an alkyl or aryl group, according to which process:
a) a 5-nitrobenzofuran derivative of formula II is hydrogenated in the presence of palladium-on-charcoal as catalyst and in an ether or a mixture of ethers as solvent, in order to form a reaction medium comprising a 5-amino-benzoyl-benzofuran derivative of formula I above, in the free base form,
b) the reaction medium comprising the 5-amino-benzoyl-benzofuran derivative of formula I in the free base form obtained above is directly treated with a halide of general formula:

$$\text{Hal-}R_3 \qquad \text{IV}$$

in which Hal represents a halogen, such as chlorine, and $R_3$ has the same meaning as above, in the presence of a basic agent, in order to obtain the desired compounds in the free base form, which are reacted, if necessary, with an organic or inorganic acid in order to form a pharmaceutically acceptable salt of this desired compound.

Subsequently, the pharmaceutically acceptable salt of the compound of formula III can be recovered from its formation medium, for example by crystallization.

In formula III above, $R_3$ represents in particular a linear or branched $C_1$-$C_8$ alkyl group, in particular a linear or branched $C_1$-$C_4$ alkyl group, such as methyl, ethyl, n-propyl, isopropyl, n-butyl or tert-butyl, or else a substituted or unsubstituted phenyl group.

According to one embodiment, $R_1$ represents n-butyl, $R_2$ represents 3-[di(n-butyl)amino]propoxy and $R_3$ represents methyl in formula III above.

The hydrogenation according to the invention is normally carried out in an ether or a mixture of ethers as solvent, in contrast to the state of the art, where this type of reaction is generally carried out in an alcohol. This reduction in an ether or a mixture of ethers makes possible in particular a better chemoselectivity of the nitro functional group at the expense of the ketone functional group which is also present and which is itself also capable of a reduction to give alcohol. This selective reduction of the nitro functional group consequently avoids the isolation of the compound of formula I in whatever way this is done, in particular by conversion of this compound, obtained in basic form, into a salt which can be easily separated from its formation medium.

The ether used as solvent is usually a dialkyl ether, such as methyl tert-butyl ether, or a cyclic ether, for example tetrahydrofuran, while the mixture of ethers generally corresponds to a mixture of dialkyl ether and of cyclic ether, for example a mixture of methyl tert-butyl ether and of tetrahydrofuran.

The methyl tert-butyl ether/THF mixture represents a solvent which is particularly preferred in the context of the present invention, in particular for the preparation of Compound A and subsequently of dronedarone.

Usually, the hydrogenation catalyst consists of palladium-on-charcoal having a water content, for example, of from 50% to 65% and more particularly from 60% to 65%. In this form, this catalyst will be used in a proportion of from 1% to 10% by weight relative to the weight of compound of formula II, for example from 1% to 5% weight/weight, more particularly 4% weight/weight. In addition, this palladium-non-charcoal having a water content may be used directly or after having been suspended in water so as to promote its dispersion in the reaction medium.

The hydrogenation, for its part, can take place at ambient temperature. However, said hydrogenation is generally carried out by heating the reaction medium at a temperature ranging up to, for example, 50-60° C., more particularly at a temperature of 40° C. This hydrogenation is usually carried out under a pressure of from 0.1 to 5 bar, in particular from 0.2 to 1 bar, more particularly at 0.2 bar.

According to one embodiment, the hydrogenation according to the invention is carried out starting from a 30% to 35% by weight solution of compound of formula II in methyl tert-butyl ether or tetrahydrofuran or in a mixture of these two ethers, this hydrogenation being carried out at a temperature of 40° C., under a pressure of 0.2 bar, and in the presence, relative to the weight of compound of formula II, of 4% by weight of palladium-on-charcoal at 5% having a water content between 60% and 65%, particularly of 64%, or of this same palladium-on-charcoal in suspension in water. Under these conditions, the increase in temperature of the reaction medium is carried out by heating from 20° C. to 40° C. over the course of one hour under a hydrogen pressure.

According to one of its specific aspects, the invention additionally relates to a process for the preparation of 2-(n-butyl)-3-(4-{3-[di(n-butyl)amino]propoxy}benzoyl)-5-aminobenzofuran, according to which 2-(n-butyl)-3-(4-{3-[di(n-butyl)amino]propoxy}benzoyl)-5-nitrobenzofuran is hydrogenated in the presence of palladium-on-charcoal as catalyst and in methyl tert-butyl ether, tetrahydrofuran or a mixture of methyl tert-butyl ether and of tetrahydrofuran as solvent, to form 2-(n-butyl)-3-(4-{3-[di(n-butyl)amino]propoxy}benzoyl)-5-aminobenzofuran in the free base form.

Moreover, according to another of its specific aspects, the invention relates to a process for the preparation of 2-(n-butyl)-3-(4-{3-[di(n-butyl)amino]propoxy}benzoyl)-5-(methanesulfonamido)benzofuran or dronedarone and of its pharmaceutically acceptable salts, according to which process:
a) 2-(n-butyl)-3-(4-{3-[di(n-butyl)amino]propoxy}benzoyl)-5-nitrobenzofuran is hydrogenated in the presence of palladium-on-charcoal as catalyst and in methyl tert-butyl ether, tetrahydrofuran or a mixture of methyl tert-butyl ether and of tetrahydrofuran as solvent, to form a reaction medium comprising 2-(n-butyl)-3-(4-{3-[di(n-butyl)amino]propoxy}benzoyl)-5-aminobenzofuran in the free base form,
b) the reaction medium comprising the 2-(n-butyl)-3-(4-{3-[di(n-butyl)amino]propoxy}benzoyl)-5-aminobenzofuran in the free base form obtained above is directly treated with a methanesulfonyl halide in the presence of a basic agent, in order to obtain the dronedarone in the basic form, which is reacted, if necessary, with an organic or inorganic acid in order to form a pharmaceutically acceptable salt of dronedarone.

Subsequently, the pharmaceutically acceptable salt of dronedarone can be recovered from its formation medium, for example by crystallization.

In the light of the preceding description, the combination formed by a 5-nitrobenzofuran derivative of formula II, palladium-on-charcoal and an ether or a mixture of ethers as solvent proves to be particularly advantageous as reaction medium for the preparation of various compounds, in particular the compounds of formula I and those of formula III above.

Consequently, another subject of the invention relates to a reaction medium, characterized in that it is formed:
a) of a 5-nitrobenzofuran derivative of formula II, in particular a derivative of formula II in which $R_1$ represents n-butyl and $R_2$ represents 3-[di(n-butyl)amino]propoxy, b) of palladium-on-charcoal,
c) of an ether, such as methyl tert-butyl ether, or of a mixture of ethers, such as a mixture of methyl tert-butyl ether and of tetrahydrofuran, as solvent.

The following non-limiting examples illustrate the preparation of a compound of formula I according to the process of the invention and also its use in the synthesis of dronedarone. In these examples, the abbreviations below comprise the meanings indicated:

Pd/C: palladium-on-charcoal
MTBE: methyl tert-butyl ether
THF: tetrahydrofuran
T: temperature
h: hours
n.i.: not identified
w/w: weight/weight
ppm: parts per million

EXAMPLES

A1) 2-(n-Butyl)-3-(4-{3-[di(n-butyl)amino]propoxy}benzoyl)-5-aminobenzofuran (Compound A or Compound of Formula I: $R_1$=n-$C_4H_9$; $R_2$=3-[di(n-butyl)amino]propoxy)

3.14 kg of 2-(n-butyl)-3-(4-{3-[di-(n-butyl)amino]propoxy}benzoyl)-5-nitrobenzofuran (compound of formula II) at 32% in solution in methyl tert-butyl ether as solvent, and 2.5% weight/weight of palladium-on-charcoal (Pd/C) having a Pd content of 5% and a water content of 50%, are charged, at 20° C., to a hydrogenation apparatus. At the same temperature, the reactor is then purged with nitrogen and hydrogen and then, with stirring, hydrogen under a pressure of 1 bar is introduced, thereby causing an exothermic reaction. The temperature of the reaction medium is raised to 40° C. over the course of 1 hour and is maintained at this temperature for 7 to 8 hours. During this period, the progression of the reaction is verified by liquid chromatography until the starting nitro derivative has disappeared. If necessary, the hydrogenation is continued for a further hour at 40° C. As soon as the reaction has ended, the reactor is purged with nitrogen and then the catalyst is filtered off and rinsed a first time with 0.79 kg of methyl tert-butyl ether and a second time with the same amount of methyl tert-butyl ether. The solution obtained (4.09 kg) is then concentrated at 40° C. under a vacuum of 250 mmHg, which gives a residual volume of 1.5 l. The concentrate is then diluted by adding 2.18 kg (2.45 vol) of tetrahydrofuran so as to obtain a solution of the desired compound in a mixture of methyl tert-butyl ether and of tetrahydrofuran. Estimated yield: 99%

According to one variant of the method described in example A1) above, Compound A was prepared as follows:

A2) 2-(n-Butyl)-3-(4-{3-[di(n-butyl)amino]propoxy}benzoyl)-5-aminobenzofuran (Compound A or compound of formula I: $R_1$=n-$C_4H_9$; $R_2$=3-[di(n-butyl)amino]propoxy)

3.14 kg of 2-(n-butyl)-3-(4-{3-[di-(n-butyl)amino]propoxy}benzoyl)-5-nitrobenzofuran (compound of formula II) at a concentration of 35% w/w in solution in methyl tert-butyl ether and tetrahydrofuran (1v/2v) as solvent, and 1.44% weight/weight of palladium-on-charcoal (Pd/C) having a Pd content of 5% and a water content of 50%, are charged, at 20° C., to a hydrogenation apparatus. At the same temperature, the reactor is then purged with nitrogen and hydrogen and then, with stirring, hydrogen under a pressure of 0.2 bar relative is introduced, thereby causing an exothermic reaction. The temperature of the reaction medium is raised to 40° C. over the course of 1 hour and is maintained at this temperature for 3 to hours. During this period, the progression of the reaction is verified by liquid chromatography until the starting nitro derivative has disappeared. If necessary, the hydrogenation is continued for a further hour at 40° C. As soon as the reaction has ended, the reactor is cooled to 20° C. and is purged with nitrogen before filtering off the catalyst, which is rinsed with 2.22 kg of tetrahydrofuran.

Estimated yield: 99%

Other tests were carried out starting from a solution of 30% to 35% of 2-(n-butyl)-3-(4-{3-[di-(n-butyl)amino]propoxy}benzoyl)-5-nitrobenzofuran using as catalyst Pd/C at 5% having a water content of 64%.

The following results were recorded:

| Pd/C % (w/w) | T (° C.) | $H_2$ Pression (bar) | Time (h) | Compound A purity (%) (HPLC) | Impurity content Y* (%) |
|---|---|---|---|---|---|
| a) Solvent: MTBE | | | | | |
| 2.5 | 40 | 1 | 6 | 98.2 | 0.23 |
| 2.5 | 40 | 1 | 7 | 98.4 | 0.55 |
| 2.5 | 40 | 1 | 9 | 98.3 | 0.20 |
| 4 | 40 | 1 | 7 | 98.6 | 0.37 |
| 5 | 40 | 0.5 | 4 | 98.3 | 0.54 |
| 10 | 20 | 1 | 12 | 97.4 | 0.59 |
| 10 | 40 | 1 | 3 | 98.1 | 0.88 |
| b) Solvent: THF | | | | | |
| 4 | 40 | 1 | 6 | 98.0 | 0.24 |
| 4 | 60 | 1 | 5 | 97.0 | 0.06 |
| c) Solvent: THF/MTBE: 1/2 (vol/vol) (suspension in water) | | | | | |
| 4 | 40 | 1 | 5 | 98.02 | 0.18 |
| d) Solvent: THF/MTBE: 2/1 (vol/vol) | | | | | |
| 3.6 | 40 | 1 | 7 | 98.4 | 0.19 |
| 3.6 | 30 | 1 | 10 | 98.7 | 0.26 |

Y*: 2-(n-butyl)-3-(4-{3-[di-(n-butyl)amino]propoxy}-1-hydroxymethyl)-5-aminobenzofuran B) Dronedarone hydrochloride (hydrochloride of the Compound of Formula III: $R_1$=n-$C_4H_9$; $R_2$=3-[di(n-butyl)amino]propoxy; $R_3$=$CH_3$)

The solution of Compound A in a mixture of methyl tert-butyl ether and of tetrahydrofuran obtained in step A1) or A2) above is charged to a reactor at ambient temperature. 0.21 kg of methanesulfonyl chloride is then added, with stirring, over the course of 1 hour, while maintaining the temperature of the reaction medium below 30° C. The mixture is cooled to 25° C. and then 0.15 kg of a 20% aqueous ammonia solution are run in, over the course of 20 min, the temperature of the reaction medium being maintained at 25° C. (+/−5° C.). 0.15 kg of methanesulfonyl chloride is again added to the reaction medium maintained at a temperature of 30° C. At the end of the addition, the temperature is adjusted and then 0.16 kg of a 20% aqueous ammonia solution is again, over the course of 20 min, run into the reaction medium maintained at 30° C. The end of the reaction is verified by liquid chromatography. If the Compound A content is greater than 2%, 0.19 kg of a 20% aqueous ammonia solution is again run in over the course of 20 min. 0.6 kg of water and 0.18 kg of methyl tert-butyl ether are then added to the reaction medium, maintained at 30° C., and stirring is maintained for 15 min. After separation by settling out, 0.7 kg of methyl tert-butyl ether is added to the organic phase (T° of the reaction medium: 28° C.) and then said phase is washed, at a temperature of 23° C., first with a solution of 0.24 kg of sodium chloride in 1.7 kg of water and then with 1 kg of water. Stirring is maintained at 28° C. for 10 min and then separation by settling out is performed. The organic phase is again washed with a solution of 0.24 kg of sodium chloride in 1.7 kg of water and then with 0.7 kg of water. Separation by settling out is performed and concentration is carried out at 45° C. under vacuum. 1.9 kg of isopropanol are then added and the mixture is concentrated at 50° C. under vacuum. 3.14 kg of isopropanol are again added and the mixture is again concentrated at 50° C. under vacuum. The reaction medium is adjusted to 4 l by addition of 1.9 kg of isopropanol, so as to obtain 3.4 kg of a solution, in isopropanol, of the desired compound in the base form. This solution is heated to 50° C., with stirring, and then 0.21 kg of hydrochloric acid is added to the reaction medium at a temperature of 50° C. to 55° C. Rinsing is carried out with isopropanol (T° of the reaction medium: 50° C.-55° C.) and then the crystallization of the desired hydrochloride is initiated by adding 0.01 kg of dronedarone hydrochloride to the reaction medium maintained at 50° C.-52° C. The resulting product is then filtered and the filtration cake is washed with 1.5 kg of isopropanol, which gives 1.3 kg of the desired hydrochloride which is dried at 45° C. under vacuum so as to obtain 1 kg of dry dronedarone hydrochloride.

Overall yield (with respect to the compound I): 96%.

Another test carried out starting from 37.6 g of Compound A isolated from its reaction medium gave dronedarone hydrochloride with a 99.6% yield of crude desired compound.

Yield calculated starting from this 5-nitrobenzofuran derivative: 93.8%.

The process according to the invention exhibits indisputable advantages in comparison with the method described in patent EP 0 471 609 or patent application WO 2002/048078.

Indeed, the quality of the compound of formula I in the base form is found to be significantly improved since the formation of fewer different impurities and a lower impurity content are recorded. This advantage makes it possible to avoid the preparation and the isolation of the oxalate of the compound of formula I, which operation presents numerous problems on the industrial scale, in particular problems of filtration and industrial hygiene during unloading.

Furthermore, the process according to the invention has the following additional advantages compared with the prior art:
1. the preparation of the 5-nitrobenzofuran derivative of formula II, in particular the preparation of 2-(n-butyl)-3-(4-{3-[di(n-butyl)amino]propoxy}benzoyl)-5-nitrobenzofuran, requires, at the end of synthesis, an extraction with methyl tert-butyl ether that must replaced with ethanol in order to tackle the subsequent hydrogenation phase in the presence of platinum oxide. The process according to the invention makes it possible to eliminate this change of solvent and thus to save time (between 8 and 16 h);
2. palladium-on-charcoal proves to be less expensive and more readily available commercially than platinum oxide;
3. the release of the compound of formula I, in particular the release of Compound A, in the base form, and the associated aqueous washes can be eliminated. The use of the non-isolated compounds of formula I in a process for the preparation of the pharmacologically active aminoalkoxy-benzoyl-benzofuran derivatives of patent EP 0 471 609 and in particular in a process for the preparation of the compounds of formula III above makes it possible to very significantly improve the overall yield of this process. In the specific case of dronedarone, the overall yield of its synthesis, starting from its corresponding 5-nitrobenzofuran derivative, rises from 60%, according to the state of the art, to at least 93% by the use of the chemoselective process of the invention. This improvement is related in particular to the absence of isolation of the oxalate of the compound of formula I and to the losses associated therewith. Consequently, the advantages conferred by the process according to the invention result in a gain in productivity, i.e. an increase in the ratio between the production and the resources used in order to obtain it. Indeed, on the one hand, for the production, a significant increase in overall yield and a reduction in the preparation time for dronedarone are obtained (improvement in the purity of the compound I, elimination of an oxalate preparation step and of an isolation step). On the other hand, for the resources used, a reduction in production costs, via in particular a reduction in investment costs, since oxalate isolation requires additional equipment, a reduction in machine running time and in operator working time (two fewer steps) and a reduction in raw material costs, for instance the catalyst for the hydrogenation, are obtained.

The invention claimed is:

1. A process for the preparation of 5-amino-benzoyl-benzofuran compounds of formula:

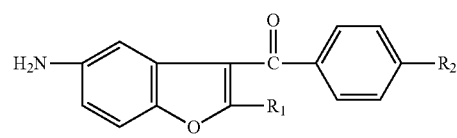

in which $R_1$ represents hydrogen or an alkyl or aryl group and $R_2$ represents hydrogen or an alkyl, alkoxy or dialkylaminoalkoxy group, comprising hydrogenating a 5-nitrobenzofuran compound of formula:

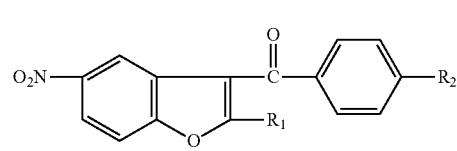

in which $R_1$ and $R_2$ have the same meanings as above, in the presence of a palladium-on-charcoal catalyst and in a solvent comprising an ether or a mixture of ethers.

2. A process for the preparation of sulfonamidobenzofuran compounds of formula:

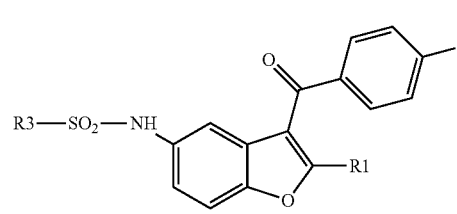

or a pharmaceutically acceptable salt thereof, in which $R_1$ represents hydrogen or an alkyl or aryl group, $R_2$ represents hydrogen or an alkyl, alkoxy or dialkylaminoalkoxy group and $R_3$ represents an alkyl or aryl group, comprising:
a) hydrogenating a 5-nitrobenzofuran compound of formula:

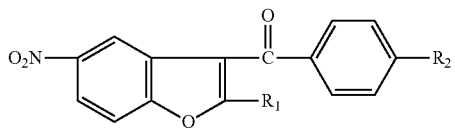

II in which $R_1$ and $R_2$ have the same meanings as above, in the presence of a palladium-on-charcoal catalyst and in a solvent comprising an ether or a mixture of ethers to form a reaction medium comprising a 5-amino-benzoyl-benzofuran compound, in the free base form, of formula:

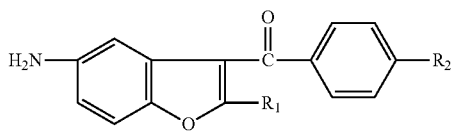

I in which $R_1$ and $R_2$ have the same meanings as above,
b) treating said reaction medium with a halide of formula:

Hal-SO$_2$R$_3$   IV in which Hal represents a halogen and $R_3$ has the same meaning as above, in the presence of a basic agent, and forming the sulfonamidobenzofuran compound of formula III in the free base form, and optionally reacting the formed compound with an organic or inorganic acid in order to form a pharmaceutically acceptable salt thereof.

3. The process as claimed in claim 1, wherein:
$R_1$ represents a linear or branched $C_1$-$C_8$ alkyl group or a phenyl group, and
$R_2$ represents a linear or branched $C_1$-$C_8$ alkyl group, a linear or branched $C_1$-$C_8$ alkoxy group or a dialkylaminoalkoxy group in which each linear or branched alkyl group is a $C_1$-$C_8$ alkyl group and the linear or branched alkoxy group is a $C_1$-$C_8$ alkoxy group.

4. The process as claimed in claim 1, wherein:
$R_1$ represents a linear or branched $C_1$-$C_4$ alkyl group, and
$R_2$ represents a linear or branched $C_1$-$C_4$ alkyl group, a linear or branched $C_1$-$C_4$ alkoxy group or a dialkylaminoalkoxy group in which each linear or branched alkyl group is a $C_1$-$C_4$ alkyl group and the linear or branched alkoxy group is a $C_1$-$C_4$ alkoxy group.

5. The process as claimed in claim 1 wherein $R_1$ represents n-butyl, and $R_2$ represents 3-[di(n-butyl)amino]propoxy.

6. The process as claimed in claim 1 wherein the ether is a dialkyl ether, a cyclic ether or a mixture thereof.

7. The process as claimed in claim 6, wherein the dialkyl ether is methyl tert-butyl ether and the cyclic ether is tetrahydrofuran.

8. The process as claimed in claim 1 wherein the catalyst, which consists of palladium-on-charcoal having a water content, is used in a proportion of from 1% to 10% by weight relative to the weight of compound of formula II.

9. The process as claimed in claim 8, wherein the palladium-on-charcoal having a water content is used in the form of a suspension in water.

10. The process as claimed in claim 1 wherein the hydrogenation takes place at a temperature ranging from ambient temperature to 50-60° C.

11. The process as claimed in claim 1 wherein the hydrogenation takes place under a pressure of from 0.1 to 5 bar.

12. The process as claimed in claim 1 wherein 2-(n-butyl)-3-(4-{3-[di(n-butyl)amino]propoxy}benzoyl)-5-nitrobenzofuran is hydrogenated in the presence of palladium-on-charcoal as catalyst and in methyl tert-butyl ether, tetrahydrofuran or a mixture of methyl tert-butyl ether and tetrahydrofuran as solvent, to form 2-(n-butyl)-3-(4-{3-[di(n-butyl)amino]propoxy}benzoyl)-5-aminobenzofuran in the free base form.

13. A reaction medium, comprising:
a) a 5-nitrobenzofuran compound of formula:

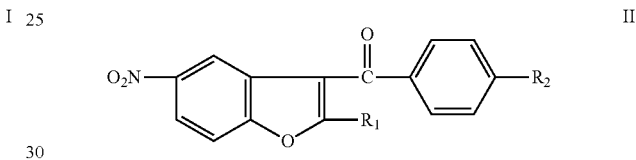

II in which $R_1$ represents hydrogen or an alkyl or aryl group and $R_2$ represents hydrogen or an alkyl, alkoxy or dialkylaminoalkoxy group,
b) palladium-on-charcoal, and
c) an ether or a mixture of ethers, as solvent.

14. The reaction medium as claimed in claim 13, wherein $R_1$ represents n-butyl and $R_2$ represents 3-[di(n-butyl)amino]propoxy.

15. The process as claimed in claim 2, wherein:
$R_1$ represents a linear or branched $C_1$-$C_8$ alkyl group or a phenyl group,
$R_2$ represents a linear or branched $C_1$-$C_8$ alkyl group, a linear or branched $C_1$-$C_8$ alkoxy group or a dialkylaminoalkoxy group in which each linear or branched alkyl group is a $C_1$-$C_8$ alkyl group and the linear or branched alkoxy group is a $C_1$-$C_8$ alkoxy group, and
$R_3$ represents a linear or branched $C_1$-$C_8$ alkyl group or a phenyl group.

16. The process as claimed in claim 2 wherein:
$R_1$ represents a linear or branched $C_1$-$C_4$ alkyl group,
$R_2$ represents a linear or branched $C_1$-$C_4$ alkyl group, a linear or branched $C_1$-$C_4$ alkoxy group or a dialkylaminoalkoxy group in which each linear or branched alkyl group is a $C_1$-$C_4$ alkyl group and the linear or branched alkoxy group is a $C_1$-$C_4$ alkoxy group, and
$R_3$ represents a linear or branched $C_1$-$C_4$ alkyl group.

17. The process as claimed in claim 2, wherein $R_1$ represents n-butyl, $R_2$ represents 3-[di(n-butyl)amino]propoxy and $R_3$ represents methyl.

18. The process as claimed in claim 2 wherein the ether is a dialkyl ether, a cyclic ether or a mixture thereof.

19. The process as claimed in claim 18, wherein the dialkyl ether is methyl tert-butyl ether and the cyclic ether is tetrahydrofuran.

20. The process as claimed in claim 2 wherein the catalyst, which consists of palladium-on-charcoal having a water content, is used in a proportion of from 1% to 10% by weight relative to the weight of compound of formula II.

21. The process as claimed in claim 20, wherein the palladium-on-charcoal having a water content is used in the form of a suspension in water.

22. The process as claimed in claim 2 wherein the hydrogenation takes place at a temperature ranging from ambient temperature to 50-60° C.

23. The process as claimed in claim 2 wherein the hydrogenation takes place under a pressure of from 0.1 to 5 bar.

24. The process as claimed in claim 2 wherein 2-(n-butyl)-3-(4-{3-[di(n-butyl)amino]propoxy}benzoyl)-5-nitrobenzofuran is hydrogenated in the presence of palladium-on-charcoal as catalyst and in methyl tert-butyl ether, tetrahydrofuran or a mixture of methyl tert-butyl ether and tetrahydrofuran as solvent, to form 2-(n-butyl)-3-(4-{3-[di(n-butyl)amino]propoxy}benzoyl)-5-aminobenzofuran in the free base form.

25. The process as claimed in claim 2 wherein said sulfonamidobenzofuran compound is 2-(n-butyl)-3-(4-{3-[di(n-butyl)amino]propoxy}benzoyl)-5-(methanesulfonamido)benzofuran or a pharmaceutically acceptable salt thereof, the process comprising:

a) hydrogenating 2-(n-butyl)-3-(4-{3-[di(n-butyl)amino]propoxy}benzoyl)-5-nitrobenzofuran in the presence of palladium-on-charcoal as catalyst and in methyl tert-butyl ether or a mixture of methyl tert-butyl ether and tetrahydrofuran as solvent, to form a reaction medium comprising 2-(n-butyl)-3-(4-{3-[di(n-butyl)amino]propoxy}benzoyl)-5-aminobenzofuran in the free base form, and b) treating said reaction medium with a methanesulfonyl halide in the presence of a basic agent, in order to obtain 2-(n-butyl)-3-(4-{3-[di(n-butyl)amino]propoxy}benzoyl)-5-(methanesulfonamido)benzofuran in the basic form, which is optionally reacted with an organic or inorganic acid in order to form a pharmaceutically acceptable salt thereof.

* * * * *